(12) United States Patent
Miyawaki et al.

(10) Patent No.: US 7,897,385 B2
(45) Date of Patent: Mar. 1, 2011

(54) FLUORESCENT PROTEIN

(75) Inventors: Atsushi Miyawaki, Saitama (JP); Ryoko Ando, Saitama (JP); Hideaki Mizuno, Saitama (JP); Satoshi Karasawa, Tokyo (JP)

(73) Assignee: Riken, Saitama (JP)

( * ) Notice: Subject to any disclaimer, the term of this patent is extended or adjusted under 35 U.S.C. 154(b) by 365 days.

(21) Appl. No.: 11/569,275

(22) PCT Filed: May 20, 2005

(86) PCT No.: PCT/JP2005/009720
§ 371 (c)(1),
(2), (4) Date: Aug. 19, 2008

(87) PCT Pub. No.: WO2005/113772
PCT Pub. Date: Dec. 1, 2005

(65) Prior Publication Data
US 2009/0155888 A1  Jun. 18, 2009

(30) Foreign Application Priority Data
May 20, 2004  (JP) ................................ 2004-150607

(51) Int. Cl.
*C12N 5/00* (2006.01)
*C07K 14/00* (2006.01)
*C07H 21/04* (2006.01)

(52) U.S. Cl. ................... 435/325; 435/252.3; 435/254.1; 435/410; 530/350; 536/23.1

(58) Field of Classification Search .................. None
See application file for complete search history.

(56) References Cited

U.S. PATENT DOCUMENTS

| | | | |
|---|---|---|---|
| 6,046,925 | A | 4/2000 | Tsien et al. |
| 2003/0092884 | A1 | 5/2003 | Lukyanov et al. |
| 2003/0157643 | A1 | 8/2003 | Almond et al. |
| 2005/0032085 | A1 | 2/2005 | Labas et al. |

FOREIGN PATENT DOCUMENTS

| | | |
|---|---|---|
| WO | 98/47148 | 10/1998 |
| WO | 02/096924 | 12/2002 |
| WO | 03/042401 | 5/2003 |

OTHER PUBLICATIONS

Supplementary material of seven pages for the IDS reference Ando et al. Sience Nov. 19, 2004, vol. 306, pp. 1370-1373.*
Habuchi et al., "Reversible single-molecule photoswitching in the GFP-like fluorescent protein Dronpa," Proceedings of the National Academy of Sciences of the United States of America, vol. 102, No. 27, Jul. 2005, pp. 9511-9516, XP002476316, ISSN: 0027-8424.
Kelmanson IV et al., Mol. Biol. Evol., vol. 20, No. 7, (2003), pp. 1125-1133.
Lesser, M. et al., The DDBJ/GenBank/EMBL databases [online], Jul. 20, 2001, Accession No. AF401282.
Matz, M. et al., The DDBJ/GenBank/EMBL databases [online], May 30, 2001, Accession No. AY037766.
Ando et al., "Regulated Fast Nucleocytoplasmic Shuttling Observed by Reversible Protein Highlighting." Science, vol. 306, No. 5700, Nov. 19, 2004, pp. 1370-1373.
Tsien, R.Y. et al., Ann. Rev. Biochem., 67, (1998), pp. 509-544.
Miyawaki, Cell Structure and Function, vol. 27, No. 5 (2002) pp. 343-347.
Labas et al., Proc. Nat. Acad. Sci. USA (PNAS), vol. 99, No. 7 (2002) pp. 4256-4261.
Japanese Office Action mailed Nov. 16, 2010 with partial English translation.

* cited by examiner

*Primary Examiner* — Nashaat T Nashed

(57) ABSTRACT

The object of the present invention is to provide a novel fluorescent protein in which on and off of fluorescence thereof can be controlled by irradiation with lights of two different wavelengths. The present invention provides a fluorescent protein shown in the following (a) or (b);
(a) a protein which has the amino acid sequence shown in SEQ ID NO: 3 or 7; or
(b) a protein which has an amino acid sequence comprising a deletion, substitution, and/or addition of one or several amino acids with respect to the amino acid sequence shown in SEQ ID NO: 3 or 7, and which has fluorescence characteristics of exhibiting a photochromic effect.

6 Claims, 6 Drawing Sheets

FLUORESCENT PROTEIN

TECHNICAL FIELD

The present invention relates to a novel fluorescent protein in which appearance and disappearance of fluorescence can be controlled by irradiation with lights of two different wavelengths. More specifically, the present invention relates to a novel fluorescent protein derived from an *Echinophylia* sp. and a novel fluorescent protein monomerized by introducing mutation into the aforementioned fluorescent protein derived from the *Echinophylia* sp. as well as use thereof.

BACKGROUND ART

Green fluorescent protein (GFP) derived from a jelly fish, *Aequorea victoria*, has many uses in biological systems. Recently, various GFP mutants that are changed in color, improved in folding characteristic, enhanced in luminance, and modified in pH sensitivity have been prepared based on random mutagenesis techniques and semi-rational mutagenesis techniques. Using genetic manipulation technology, another protein is fused to a fluorescent protein such as GFP, and monitoring of its expression and transport are being carried out.

As one of the most frequently used GFP mutants, yellow fluorescent protein (YFP) is listed. YFP shows fluorescence with the longest wavelength among jellyfish *Aequorea* GFP mutants. The values of $\epsilon$ and $\Phi$ of most YFPs are 60,000 to 100,000 $M^{-1}cm^{-1}$ and 0.6 to 0.8, respectively (Tsien, R. Y. (1998). Ann. Rev. Biochem. 67, 509-544), and these values are comparable to those of common luminophores (fluorescein, rhodamine, etc.). Accordingly, improvement in absolute luminance of YFP is almost reaching the limit.

As other examples of the GFP mutants, there is cyan fluorescent protein (CFP), and enhanced cyan fluorescent protein (ECFP) is known. Further, red fluorescent protein (RFP) is also isolated from a *Discoma* sp., and DsRed is known. Thus, four typed of fluorescent proteins (green, yellow, cyan, and red) have been developed one after another, and the spectral range has been greatly extended.

DISCLOSURE OF THE INVENTION

It is recognized that the yellow fluorescent protein (YFP) that is a modified form of GFP derived from *Aequorea victoria* tends to become gradually darker by irradiating with 488 nm light and then tends to slightly recover its fluorescence (at most 20%) by irradiating with 405 nm light. However, since the reduction in photochromism of YFP (i.e. disappearance and recovery of fluorescence) is incomplete, it is still far from practical use. The object of the present invention is to solve the above problem, and specifically, the object of the present invention is to solve the problem of providing a novel fluorescent protein in which on and off of fluorescence thereof can be controlled by irradiation with lights of two different wavelengths.

As a result of assiduous research intended to solve the above problem, the present inventors have succeeded in preparing a protein in which the above-mentioned photochromic effect can be fully realized using a novel protein derived from an *Echinophylia* sp. That is, the fluorescence intensity of the fluorescent protein of the present invention can be controlled between 0% and 100% by irradiating with 488 nm light and 405 nm light. The present invention has been achieved by these findings.

That is, the present invention provides a fluorescent protein shown in the following (a) or (b);
(a) a protein which has the amino acid sequence shown in SEQ ID NO: 1 or 5; or
(b) a protein which has an amino acid sequence comprising a deletion, substitution, and/or addition of one or several amino acids with respect to the amino acid sequence shown in SEQ ID NO: 1 or 5, and which has fluorescence characteristics.

Another aspect of the present invention provides a DNA encoding the fluorescent protein shown in the following (a) or (b);
(a) a protein which has the amino acid sequence shown in SEQ ID NO: 1 or 5; or
(b) a protein which has an amino acid sequence comprising a deletion, substitution, and/or addition of one or several amino acids with respect to the amino acid sequence shown in SEQ ID NO: 1 or 5, and which has fluorescence characteristics.

Still another aspect of the present invention provides a DNA shown in the following (a) or (b);
(a) DNA which has the nucleotide sequence shown in SEQ ID NO: 2 or 6;
(b) DNA which has a nucleotide sequence comprising a deletion, substitution, anchor addition of one or several nucleotides with respect to the nucleotide sequence shown in SEQ ID NO: 2 or 6, and which has a nucleotide sequence encoding a protein flat has fluorescence characteristics.

Still another aspect of the present invention provides a recombinant vector having the above-described DNA of the present invention.

Still another aspect of the present invention provides a transformant having the above-described DNA or recombinant vector of the present invention.

Still another aspect of the present invention provides a fluorescent protein shown in the following (a) or (b);
(a) a protein which has the amino acid sequence shown in SEQ ID NO: 3 or 7; or
(b) a protein which has an amino acid sequence comprising a deletion, substitution and/or addition of one or several amino acids with respect to the amino acid sequence shown in SEQ ID NO: 3 or 7, and which has fluorescence characteristics of exhibiting a photochromic effect.

Still another aspect of the present invention provides a DNA encoding the fluorescent protein shown in the following (a) or (b):
(a) a protein which has the amino acid sequence shown in SEQ ID NO: 3 or 7; or
(b) a protein which has an amino acid sequence comprising a deletion, substitution, and/or addition of one or several amino acids with respect to the amino acid sequence shown in SEQ ID NO: 3 or 7, and which has fluorescence characteristics of exhibiting a photochromic effect.

Still another aspect of the present invention provides a DNA shown in the following (a) or (b)
(a) DNA which has the nucleotide sequence shown in SEQ ID NO: 4 or 8;
(b) DNA which has a nucleotide sequence comprising a deletion, substitution, and/or addition of one or several nucleotides with respect to the nucleotide sequence shown in SEQ ID NO: 4 or 8, and which has a nucleotide sequence encoding a protein that has fluorescence characteristics of exhibiting a photochromic effect.

Still another aspect of the present invention provides a recombinant vector having the above-described DNA of the present invention.

Still another aspect of the present invention provides a transformant having the above-described DNA or recombinant vector of the present invention.

Still another aspect of the present invention provides a photochromic material comprising the above-described fluorescent protein of the present invention.

Still another aspect of the present invention provides an optical recording medium having a recording layer that contains the above-described fluorescent protein of the present invention and on which recording and reading of information can be performed by light irradiation.

BEST MODE FOR CARRYING OUT THE INVENTION

Figure 1:
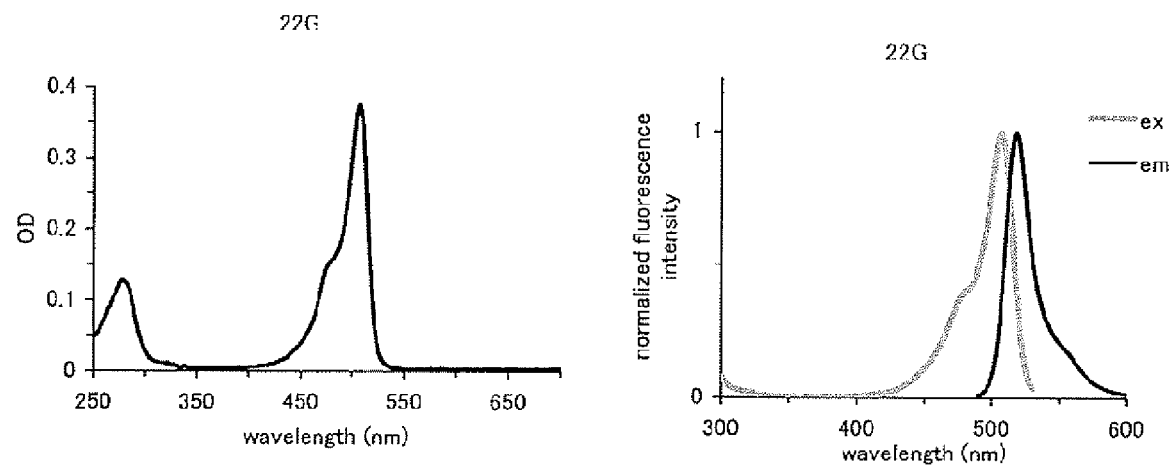
FIG. 1 shows an absorption spectrum and fluorescence and excitation spectra of 22G (SEQ ID NO: 1)

Hereinafter, embodiments of the present invention will be explained in detail.
(1) Fluorescent Protein of the Present Invention A first fluorescent protein of the present invention is a protein shown in either of the following (a) or (b):
(a) a protein which has the amino acid sequence shown in SEQ ID NO: 1 or 5; or
(b) a protein which has an amino acid sequence comprising a deletion, substitution, and/or addition of one or several amino acids with respect to the amino acid sequence shown in SEQ ID NO: 1 or 5, and which has fluorescence characteristics.

The fluorescent protein which has the amino acid sequence shown in SEQ ID NO: 1 (22G) is characterized by having the following characteristics.
(1) The wavelength of maximum absorption is 507 nm, and the wavelength of maximum fluorescence is 518 nm;
(2) The molar extinction coefficient at 507 nm is 110,000;
(3) The quantum yield is 0.67; and
(4) The pH sensitivity of the fluorescence characteristics is pKa=47.

The wavelength of maximum absorption of the fluorescent protein which has the amino acid sequence shown in SEQ ID NO: 5 (22B) is 380 nm, and the wavelength of maximum fluorescence is 467 nm.

In examples in the present specification, DNA encoding the amino acid sequence shown in SEQ ID NO: 1 among the first fluorescent proteins of the present invention was cloned using an *Echinophylia* sp. as the starting material. The *Echinophylia* sp. is a kind of coral belonging to the family Pectiniidae, order Scleractinia, subclass Hexacorallia, class Anthozoa, and phylum Cnidaria, is adherent, and often forms colonies in a shape of sheath, thin plate, or leaf. It should be noted that, in certain instances, the protein of the present invention may also be obtained from fluorescent corals other than the *Echinophylia* sp., and such a protein is also included in the scope of the present invention.

In examples in the present specification DNA encoding the amino acid sequence shown in SEQ ID NO: 3 was obtained by using DNA encoding the amino acid sequence shown in SEQ ID NO: 1 as a template, introducing mutations randomly by performing PCR in the presence of added $MnCl_2$, and then selecting from clones obtained by the introduction of random mutations.

A second fluorescent protein of the present invention is a protein shown in either of the following (a) or (b):
(a) a protein which has the amino acid sequence shown in SEQ ID NO: 3 or 7; or
(b) a protein which has an amino acid sequence comprising a deletion, substitution, and/or addition of one or several amino acids with respect to the amino acid sequence shown in SEQ ID NO: 3 or 7, and which has fluorescence characteristics of exhibiting a photochromic effect.

The fluorescent protein (m22G3) which has the amino acid sequence shown in SEQ ID NO: 3 is characterized by having the following characteristics:
(1) The wavelength of maximum absorption is 503 nm, and the wavelength of maximum fluorescence is 518 nm;
(2) The molar extinction coefficient at 503 nm is 57,000;
(3) The quantum yield is 0.62; and
(4) The pH sensitivity of the fluorescence characteristics is pKa=5.
(5) The protein has fluorescence characteristics of exhibiting a photochromic effect. Specifically, by irradiating light around the wavelength of maximum absorption of 503 nm, absorption and fluorescence are attenuated, and instead an absorption around 380 nm appears, whereas when light around 380 nm is irradiated, the absorption around 380 nm disappears, and the absorption and fluorescence around 518 nm are completely recovered.

The fluorescent protein (m3m4) which has the amino acid sequence shown in SEQ ID NO: 7 is characterized by having the following characteristics.
(1) The wavelength of maximum absorption is 486 nm, and the wavelength of maximum fluorescence is 513 nm;
(2) The molar extinction coefficient at 486 nm is 56,000;
(3) The quantum yield is 0.28; and
(4) The protein has fluorescence characteristics of exhibiting a photochromic effect.

In examples in the present specification, the DNA encoding the amino acid sequence shown in SEQ ID NO: 3 among the second fluorescent proteins of the present invention was obtained by using the DNA encoding the amino acid sequence shown in SEQ ID NO: 1 as a template, introducing mutations randomly by performing PCR in the presence of added $MnCl_2$, and then selecting DNA having a monomer size from among clones obtained by the introduction of random mutations. Further, DNA encoding the amino acid sequence shown in SEQ ID NO: 7 was obtained by using the DNA encoding the amino acid sequence shown in SEQ ID NO: 3 as a template, introducing mutations randomly by performing PCR in the presence of added $MnCl_2$, and then selecting from clones obtained by the introduction of random mutations. The second fluorescent proteins of the present invention are characterized by having fluorescence characteristics of exhibiting the photochromic effect.

The range of "one to several" in "an amino acid sequence comprising a deletion, substitution, and/or addition of one or several amino acids" referred to in the present specification is not particularly limited but means, for example, about 1 to 20, preferably 1 to 10, more preferably 1 to 7, further more preferably 1 to 5, and particularly preferably 1 to 3.

"Fluorescence characteristics" referred to in the present specification means an ability to emit fluorescence by irradiation of excitation light. The fluorescence characteristics of the fluorescent protein which has the amino acid sequence comprising a deletion, substitution, and/or addition of one or several amino acids with respect to the amino acid sequence shown in SEQ ID NO: 1 or 5 may be comparable to or different from those of the fluorescent protein which has the amino acid sequence shown in SEQ ID NO: 1 or 5. Examples of parameters of the fluorescence characteristics include fluorescence intensity, excitation wavelength, fluorescence wavelength, and pH sensitivity.

"Fluorescence characteristics of exhibiting a photochromic effect" referred to in the present specification means fluorescence characteristics in which absorption and fluorescence are attenuated or lost by irradiation of light having a predetermined wavelength such as a wavelength around the wavelength of maximum absorption and an absorption appears in a different wavelength range, and in which when light having the wavelength of the absorption that newly appeared is irradiated, the absorption and fluorescence that were attenuated or lost are recovered.

The method of obtaining the fluorescent protein of the present invention is not particularly limited, and the fluorescent protein may be a protein synthesized by chemical synthesis or a recombinant protein prepared by gene recombination technology.

When a recombinant protein is prepared, it is necessary to obtain DNA encoding the protein of interest. By using the information on the amino acid sequence shown in SEQ ID NO: 1, 3, 5, or 7 and the nucleotide sequence shown in SEQ ID NO: 2, 4, 6, or 8 in the Sequence Listing of the present specification, appropriate primers are designed, and with the use of these primers, PCR is performed using cDNA library prepared from the *Echinophylia* sp. as the template, whereby the DNA encoding the first fluorescent protein of the present invention can be obtained. Based on the DNA encoding the first fluorescent protein of the present invention, the DNA encoding the second fluorescent protein of the present invention can be obtained by introducing predetermined mutation into the DNA encoding the first fluorescent protein. When partial fragments of the DNA encoding the fluorescent protein of the present invention were obtained by the above-described PCR, DNA encoding the desired fluorescent protein can be obtained by ligating the prepared DNA fragments in order using genetic recombination technology. The fluorescent protein of the present invention can be produced by introducing this DNA into an appropriate expression system. Expression in an expression system will be described later in the present specification.

(2) DNA of the Present Invention

According to the present invention, DNAs encoding the fluorescent protein of the present invention are provided.

Specific examples of DNA encoding the first fluorescent protein of the present invention include DNA encoding the protein shown in the following (a) or (b).

(a) a protein which has the amino acid sequence shown in SEQ ID NO: 1 or 5; or
(b) a protein which has an amino acid sequence comprising a deletion, substitution, and/or addition of one or several amino acids with respect to the amino acid sequence shown in SEQ ID NO: 1 or 5, and which has fluorescence characteristics.

Further specific examples of DNA encoding the first fluorescent protein of the present invention also include the DNA shown in the following (a) or (b):
(a) DNA which has the nucleotide sequence shown in SEQ ID NO: 2 or 6;
(b) DNA which has a nucleotide sequence comprising a deletion, substitution, and/or addition of one or several nucleotides with respect to the nucleotide sequence shown in SEQ ID NO: 2 or 6, and which has a nucleotide sequence encoding a protein that has fluorescence characteristics.

Specific examples of DNA encoding the second fluorescent protein of the present invention include DNA encoding the protein shown in the following (a) or (b):
(a) a protein which has the amino acid sequence shown in SEQ ID NO: 3 or 7; or
(b) a protein which has an amino acid sequence comprising a deletion, substitution, and/or addition of one or several amino acids with respect to the amino acid sequence shown in SEQ ID NO, 3 or 7, and which has fluorescence characteristics of exhibiting a photochromic effect.

Further specific examples of DNA encoding the second fluorescent protein of the present invention also include the DNA shown in the following (a) or (b):
(a) DNA which has the nucleotide sequence shown in SEQ ID NO: 4 or 8;
(b) DNA which has a nucleotide sequence comprising a deletion, substitution, and/or addition of one or several nucleotides with respect to the nucleotide sequence shown in SEQ ID NO: 4 or 8, and which has a nucleotide sequence encoding a protein that has fluorescence characteristics of exhibiting a photochromic effect.

The range of "one to several" in "a nucleotide sequence comprising a deletion, substitution, and/or addition of one or several nucleotides" referred to in the present specification is not particularly limited but means, for example, about 1 to 50, preferably 1 to 30, more preferably 1 to 20, further more preferably 1 to 10, and particularly preferably 1 to 5.

The DNA of the present invention can be synthesized, for example, by the phosphoramidite method, and can also be produced by the polymerase chain reaction (PCR) using specific primers. The method of preparing the DNA of the present invention or the fragments thereof is as described above in the present specification.

The method of introducing a desired mutation into a predetermined nucleotide sequence is known to persons skilled in the art. For example, DNA having the mutation can be constructed by appropriately using known techniques such as site specific mutagenesis method, PCR using degenerate oligonucleotides, and exposure of cells containing the nucleic acid to a mutagen or radiation. These known techniques are described, for example, in Molecular Cloning: A Laboratory Manual, $2^{nd}$ Ed., Cold Spring Harbor Laboratory, Cold Spring Harbor, N.Y., 1989 and Current Protocols in Molecular Biology, Supplement 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent front host cells, such as a dihydrofolate reductase (DHFR) gene or a *Schizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Schizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to Filamentous fungi such as *Aspergillus, Neurospora, Fusarium* or *Trichoderma*. Where Filamentous fungi are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and S21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the protein of the present invention from the culture product of the transformant, common methods of isolating and purifying proteins may be used.

For example, where the protein of the present invention is expressed in a state dissolved in cells, after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of Fluorescent Protein of the Present Invention as Fluorescent Labeling Substance The fluorescent protein of the present invention can be used as a fluorescent labeling substance. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and J. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae, Escherichia coil* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes. Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

An appropriate filter set can be selected depending on the fluorescence wavelength of the fluorescent protein. For example, since the wavelength of maximum absorption of the fluorescent protein having the amino acid sequence shown in SEQ ID NO: 1 is 507 nm, and the wavelength of maximum fluorescence thereof is 518 nm, ca. 500 to 510 nm filter for excitation light and ca. 510 to 530 nm filter for fluorescence light can be used. Similarly, since the wavelength of maximum absorption of the fluorescent protein having the amino acid sequence shown in SEQ ID NO. 3 is 503 nm, and the wavelength of maximum fluorescence thereof is 518 nm, ca. 500 to 510 nm filter for excitation light and ca. 510 to 530 nm filter for fluorescence light can be used. Similarly, since the wavelength of maximum absorption of the fluorescent protein having the amino acid sequence shown in SEQ ID NO: 5 is 380 nm, and the wavelength of maximum fluorescence thereof is 467 nm, ca. 370 to 390 nm filter for excitation light and ca. 460 to 480 nm filter for fluorescence light can be used. Similarly, since the wavelength of maximum absorption of the fluorescent protein having the amino acid sequence shown in SEQ ID NO: 7 is 486 nm, and the wavelength of maximum fluorescence thereof is 513 nm, ca. 480 to 490 nm filter for excitation light and ca. 500 to 520 nm filter for fluorescence light can be used.

Further, when viable cells are observed with time using a fluorescence microscope, photographing should be performed in a short time, and therefore a high sensitivity cooled CCD camera is used. In the cooled CCD camera, thermal noise is reduced by cooling CCD, and very weak fluorescent images can be clearly photographed with a short-time exposure.

(6) Use of Fluorescent Protein of the Present Invention in Recordings Medium and the Like by Utilizing Photochromic Effect Further, since the second fluorescent protein of the present invention has fluorescence characteristics of exhibiting a photochromic effect (photochromic fluorescence characteristics), the second fluorescent protein of the present invention can be applied to various uses including optical recording media such as CD, DVD, holographic recording medium and smart card; display devices such as billboard, fluorescent screen, TV and computer monitor; lens; biosensor; biochip; photochromic fiber material; and the like.

The optical recording medium of the present invention can be produced by forming on a substrate a recordings layer containing the fluorescent protein having fluorescence characteristics of exhibiting a photochromic effect according to the present invention. The use of a water immersion lens in an optical system for writing and playback can make the numerical aperture (NA) larger. Owing to this, high resolution can be expected.

The material of the substrate used for the production of the optical recording medium is not particularly limited, and for example, glass, plastic, paper, and metal (acceptable in either sheet or foil form) such as aluminum are included, and particularly, plastic is preferred. The material of the plastic is also not particularly limited, and acrylic resin, methacrylic resin, vinyl acetate resin, vinyl chloride resin, nitrocellulose resin, polyethylene resin, polypropylene resin, polycarbonate resin, polyimide resin, polysulfone resin, and the like are included.

The recording layer can be formed on a substrate by dissolving the fluorescent protein of the present invention together with a binder as needed in an appropriate solvent and applying this onto the substrate so as to form a thin film having a film thickness of 1 nm to 100 μm, preferably 10 nm to 50 μm, by means of a doctor blade method, casting method, spinner method, immersion method, or the like. Examples of the binder used here include polyester, polystyrene, polyvinyl butyral, polyvinylidene chloride, polyvinyl chloride, methyl polymethacrylate, polyvinyl acetate, cellulose acetate, epoxy resin, and phenol resin. Further, examples of appropriate solvent include toluene, cyclohexanone, methyl ethyl ketone, and ethyl acetate.

The content of the fluorescent protein of the present invention in the formed thin film is not particularly limited and can be appropriately determined according to the absorbance of the fluorescent protein used, the fluorescence intensity generated, and the like. The recording layer may be provided on both surfaces or only one surface of the substrate.

Recording on the optical recording medium of the present invention produced as above can be performed by irradiating converged light onto the recording layer provided on the both surfaces or one surface of the substrate. In the irradiated area, changes in fluorescence characteristics occur by absorbing light energy, and information is recorded. Playback of the recorded intonation can be performed by reading the difference in fluorescence induced by light irradiation.

The fluorescent protein of the present invention can be applied to the field of photochromism as described, and examples of applications include those disclosed in WO98/47148 (Photochromic fluorescent proteins and optical memory storage devices based on fluorescent proteins) and WO02/96924 (Kindling fluorescent proteins and methods for their use).

The present invention is specifically explained by way of the following examples, but is not limited only to these examples.

EXAMPLES

Example 1

Isolation of Novel Fluorescent Protein Gene (22G) from Coral

A fluorescent protein gene was isolated from an *Echinophylia* sp. that emits fluorescence by the following procedures.

(1) Extraction of Total RNA

The total RNA was extracted by the acid guanidium-phenol-chloroform method. Frozen *Echinophylia* was disrupted in a denaturation solution using a Multi-Beads Shocker (Yasci Kiki Corporation). To this was added phenol/chloroform, and RNA was separated from protein-DNA complex by centrifugation. The aqueous layer containing RNA was added to isopropanol and centrifuged, thereby affording the total RNA as a precipitate.

(2) Purification of RNA

From the total RNA, mRNA was isolated by using Oligotex™-dT30 (Product of Roche Ltd.). To the total RNA, Oligotex™-dT30<super> was added, and after the secondary structure of the RNA was disrupted by heating, the RNA and Oligotex™-dT30 were allowed to bind to each other at 37° C. After washing and subsequent heating and centrifugation, supernatant containing eluted mRNA was obtained. After Oligotex-dT30 was removed, mRNA was precipitated with ethanol and NaCl, and the mRNA precipitate was dissolved in water.

(3) Synthesis of cDNA cDNA was synthesized using TimeSaver™ and Directional Cloning Toolbox™ (both produced by Amersham Pharmacia Ltd.). After the MRNA was heated to disrupt the secondary structure, DTT and NotI-dT primer (5'd (AAC TGG AAG AAT TCG CGG CCG CAG GAA $T_{18}$)p3' (SEQ ID NO:9)) were added to First-Strand Reaction Mix, so that first-strand was synthesized. Further, this was added to Second-Strand Reaction Mix to synthesize a second strand followed by purifying on an attached spun column. To the 5' end of the purified double-stranded cDNA, EcoRI adaptor was ligated, and only the 3' end was cut with NotI. This was purified once again on a spun column to obtain cDNA.

(4) Expression Cloning

The synthesized cDNA was inserted into $pRSET_B$ (product of Invitrogen Corporation) that had been provided with EcoRI and NotI sites, and this was introduced into JM109 DE3 strain of *E. coli* to prepare a library. Since proteins are synthesized in this *E. coli* strain, fluorescent protein clones can be selected depending on whether colonies emit fluorescence by irradiation of light. As the result, one positive colony was obtained from ca. 80,000 colonies and named clone 22G. Its nucleotide sequence was determined by a DNA sequencer. The amino acid sequence and the nucleotide sequence of 22G are shown in SEQ ID NOs: 1 and 2, respectively.

A protein in which His-Tag was added to the fluorescent protein 22G (SEQ ID NO: 1) was expressed using *E. coli* by a conventional method and purified with Ni-Agarose.

Example 2

Analysis of Fluorescence Characteristics of Fluorescent Protein (22G) (SEQ ID NO: 1)

(1) Absorption Spectrum and Fluorescence and Excitation Spectra

For the measurement of absorption spectrum, 50 mM HEPES (pH 7.5) solution was used. For the fluorescence and excitation spectra, 50 mM HEPES (pH 7.5) solution was used, and the fluorescence spectrum excited at 480 nm and the excitation spectrum for 540 nm fluorescence were measured. The absorption spectrum of the fluorescent protein 22G (SEQ ID NO: 1) is shown on the left of FIG. 1, and the fluorescence and excitation spectra are shown on the right of FIG. 1.

(2) Characteristics of pH Sensitivity

Figure 2:
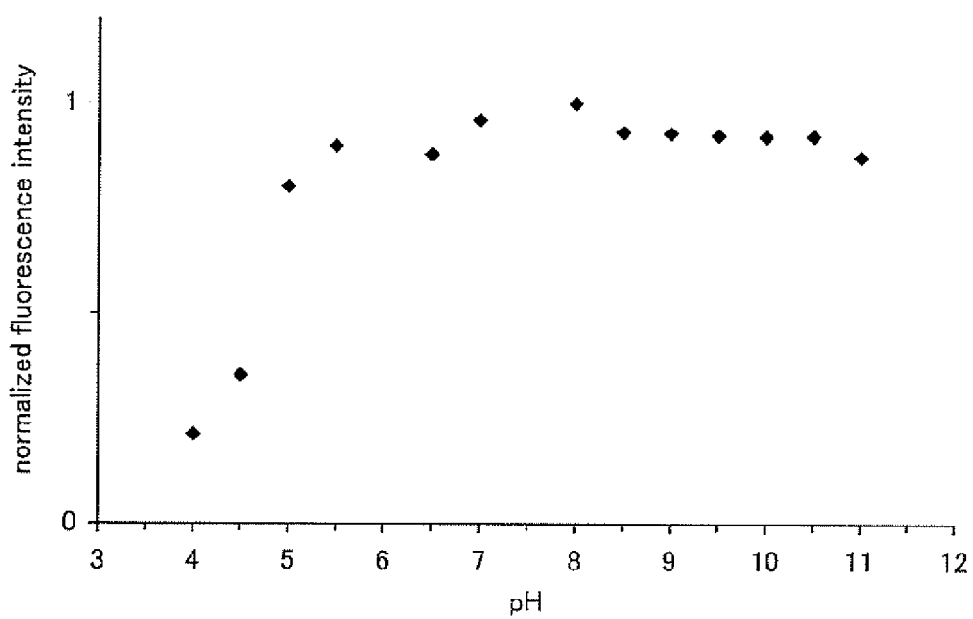
FIG. 2 shows measurement results of pH sensitivity of fluorescence intensity of 22G (SEQ ID NO: 1)

The fluorescence intensity at 518 nm excited at 480 nm was measured using the following buffers. The results are shown in FIG. 2.
pH 4, 4.5, 5, 5.5: 50 mM AcONa—AcOH
pH 6.5: 50 mM MES-NaOH
pH 7: 50 mM MOPS-KOH
pH 8, 8.5: 50 mM HEPES-NaOH
pH 9, 9.5, 10, 10.5: 50 mM glycine-NaOH
pH 11: 50 mM $Na_2HPO_4$—NaOH (3) Summary of Fluorescence Characteristics of 22G (SEQ ID NO: 1)

The properties of 22G (SEQ ID NO: 1) obtained from the above results are shown in Table 1.

TABLE 1

| Wavelength of maximum absorption | Wavelength of maximum fluorescence | Molar extinction coefficient | Quantum yield | pKa | |
|---|---|---|---|---|---|
| 507 nm | 518 nm | 110,000 (507 nm, pH 7.4) | 0.67 | 4.7 | tetramer |

Example 3

Monomerization of Fluorescent Protein (22G) (SEQ ID NO: 1)

Mutation was inserted into the fluorescent protein (22G) (SEQ ID NO: 1) obtained in Example 1 by the following procedures by random mutagenesis so as to monomerize it.

Mutations were randomly introduced by performing PCR in the presence of added $MnCl_2$ using the cloned DNA of 22G as the template. For the DNA polymerase, TAKARA Taq (product of Takara Bio Inc.) was used. A primer with a BamHI site added to the 5' side (AAG CTC CCG GAT CCG ATG AGT GTG ATT AAA CCA GAC) (SEQ ID NO: 10) and a primer with an EcoRI site added to the 3' side (ATC GTT GAA TTC TTA CTT GGC CTG CCT CGG CAG) (SEQ ID NO: 11) were used as the forward primer and the reverse primer, respectively. Amplified DNA was cut with BamHI and EcoRI and then inserted into pRSET$_B$, followed by introduction into the JM109 DE3 strain and culturing on a LA plate. Among clones obtained by the random mutagenesis, clones that produced a protein having approximately the same size as that of the monomer as revealed by pseudo-native PAGE were submitted for confirmation of molecular weight by ultracentrifugation. The nucleotide sequence of a clone containing a definitely monomerized protein was determined by a DNA sequencer and named m22G3 (SEQ ID NO: 4). The amino acid sequence and the nucleotide sequence of the monomer clone (m22G3) are shown in SEQ ID NOs: 3 and 4, respectively.

Using *E. coli*, a protein in which a His-Tag was added to the fluorescent protein m22G3 (SEQ ID NO: 3) was expressed according to a conventional method and purified with Ni-Agarose.

Example 4

Analysis of Fluorescence Characteristics of Mutant m22G3 (SEQ ID NO: 3)

(1) Absorption Spectrum and Fluorescence and Excitation Spectra

Figure 3:
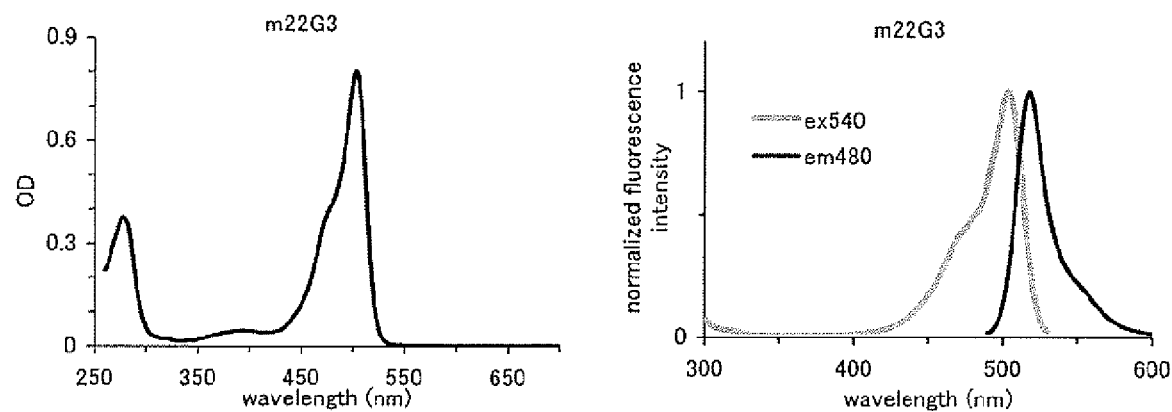
FIG. 3 shows an absorption spectrum and fluorescence and excitation spectra of m22G3 (SEQ ID NO: 3)

For the absorption spectrum, 50 mM HEPES (pH 7.5) solution was used. For the fluorescence and excitation spectra, 50 mM HEPES (pH 7.5) solution was used, and the fluorescence spectrum excited at 480 nm and the excitation spectrum for 540 nm fluorescence were measured. The absorption spectrum of the fluorescent protein m22G3 (SEQ ID NO: 3) is shown on the left of FIG. 3, and the fluorescence and excitation spectra are shown on the right of FIG. 3.

(2) Characteristics of pH Sensitivity

Figure 4:
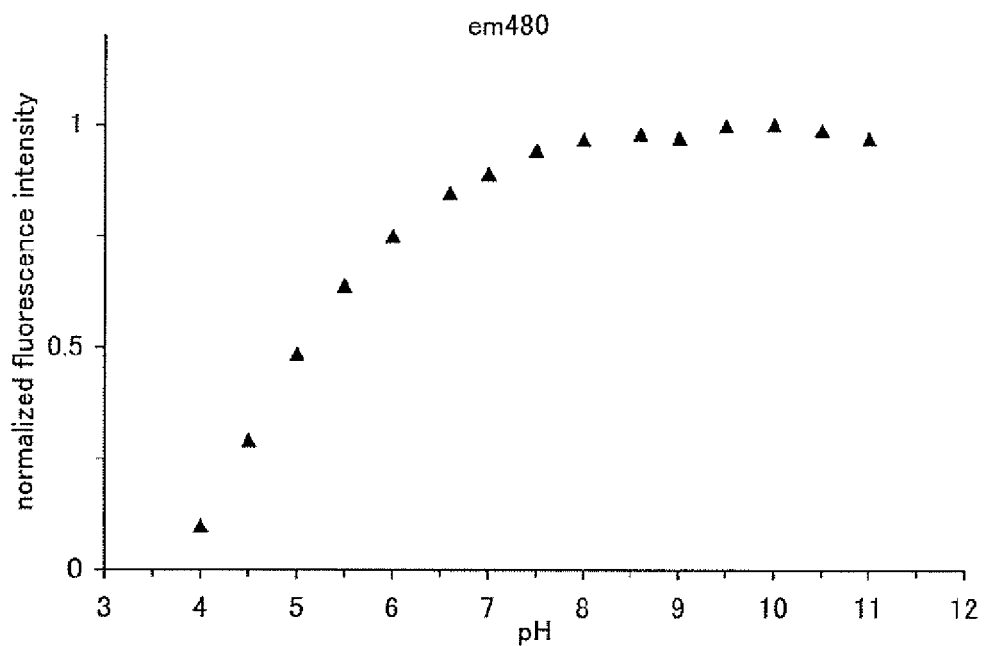
FIG. 4 shows measurement results of pH sensitivity of fluorescence intensity of m22G3 (SEQ ID NO: 3)

The fluorescence intensity at 518.5 nm excited at 480 nm was measured using the following buffers. The results are shown in FIG. 4.
pH 4, 4.5, 5, 5.5: 50 mM AcONa—AcOH
pH 6.5: 50 mM MES-NaOH
pH 7: 50 mM MOPS-KOH
pH 8, 8.5: 50 mM HEPES-NaOH
pH 9, 9.5, 10, 10.5: 50 mM glycine-NaOH
pH 11: 50 mM $Na_2HPO_4$—NaOH (3) Summary of Fluorescence Characteristics of m22G3 (SEQ ID NO: 3)

The properties of m22G3 (SEQ ID NO: 3) obtained from the above results are shown in Table 2.

TABLE 2

| Wavelength of maximum absorption | Wavelength of maximum fluorescence | Molar extinction coefficient | Quantum yield | pKa | |
|---|---|---|---|---|---|
| 503 nm | 518 nm | 57,000 (503 nm, pH 7.4) | 0.62 | 5 | monomer |

(3) Photochromic Effect of m22G3 (SEQ ID NO: 3)

Figure 5:
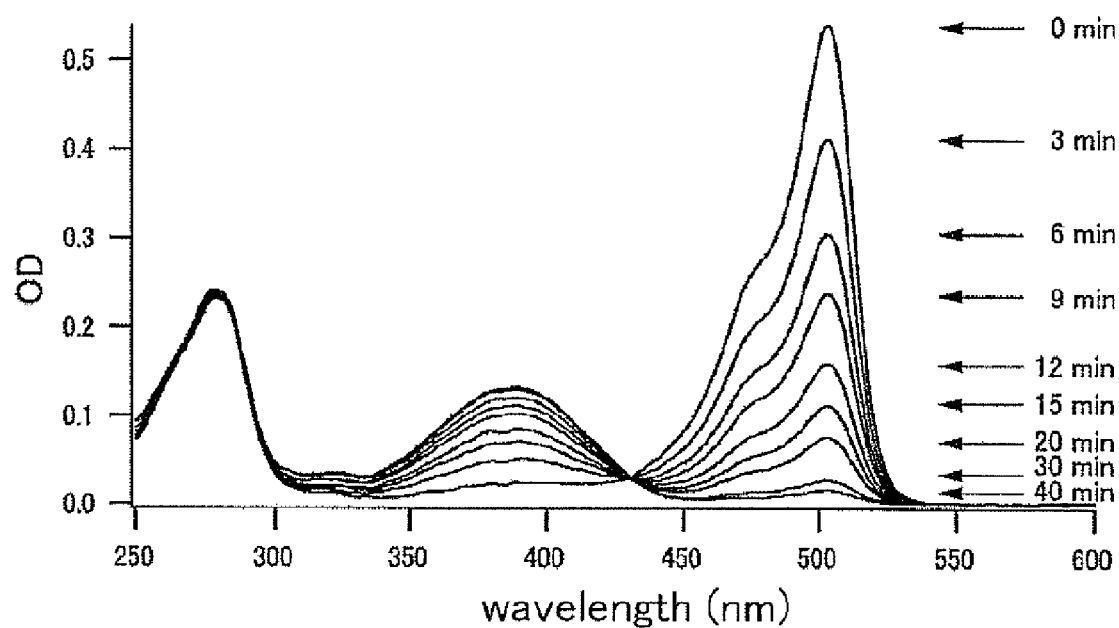
FIG. 5 is a diagram showing attenuation of absorption and fluorescence and appearance of an alternative absorption around 380 nm when light around the wavelength of maximum absorption of 503 nm is irradiated on m22G3 (SEQ ID NO: 3)
Figure 6:
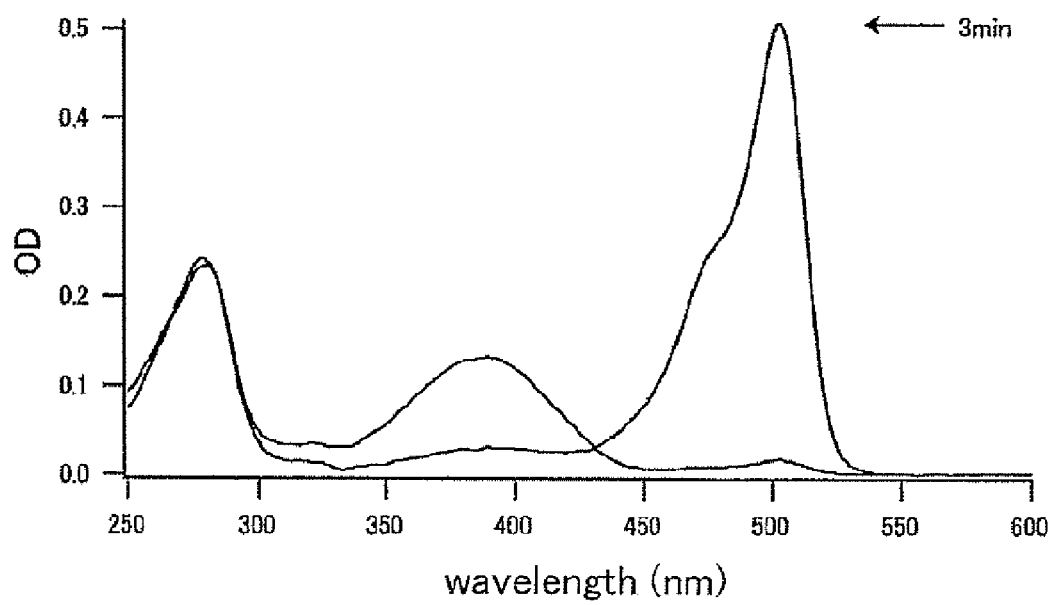
FIG. 6 is a diagram showing disappearance of the absorption at 380 nm and complete recovery of absorption and fluorescence at 518 nm when light around 380 nm is irradiated on m22G3 (SEQ ID NO: 3)

Further, characteristics of this mutant (m22G) (SEQ ID NO: 3) include its ability to exhibit photochromism. First, by irradiating light around the wavelength of maximum absorption of 503 nm, the absorption and fluorescence are attenuated, and instead an absorption around 380 nm appears (FIG. 5). On the other hand, when light around 380 nm is irradiated, the absorption around 380 nm disappears, and the absorption and fluorescence around 518 nm are completely recovered (FIG. 6). In other words, it is a great feature of this mutant m22G3 (SEQ ID NO: 3) that a bright state and a dark state are interchangeable with lights of two different wavelengths.

Example 5

Preparation of Mutant of Fluorescent Protein (22G) (SEQ ID NO: 1)

Mutation was further inserted into the fluorescent protein 22G (SEQ ID NO: 1) obtained in Example 1 according to the following procedures, and a mutant having different properties was obtained.
<Method> Random Mutagenesis Mutations were randomly introduced by performing PCR in the presence of added $MnCl_2$ using the DNA of 22G (SEQ ID NO: 2) as the template.

For the DNA polymerase, TAKARA Taq (product of Takara Bio Inc.) was used. A primer with a BamHI site added to the 5' side and a primer with an EcoRI site added to the 3' side were used as the forward primer and the reverse primer, respectively. Amplified DNA was cut with BamHI and EcoRI and then inserted into $pRSET_B$, followed by introduction into the JM109 DE3 strain and culturing on a LA plate.

Among clones obtained by the random mutagenesis, a clone having properties greatly different from those of 22G was selected, and the nucleotide sequence of the clone was determined by a DNA sequencer. This clone was named 22B. The amino acid sequence and the nucleotide sequence of 22B are shown in SEQ ID NOs: 5 and 6, respectively.

Using E. coli, a protein in which a His-tag was added to the fluorescent protein 22B (SEQ ID NO: 5) was expressed according to a conventional method and purified with Ni-Agarose.

Example 6

Analysis of Fluorescence Characteristics of Mutant 22B (SEQ ID NO: 5)

(1) Absorption Spectrum and Fluorescence and Excitation Spectra

Figure 7:
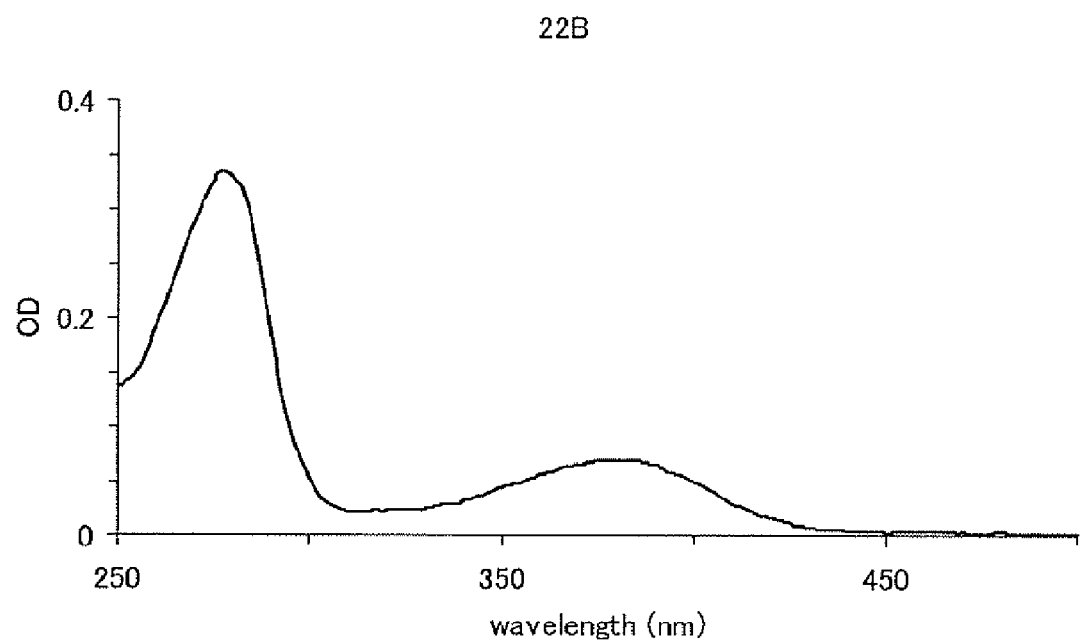
FIG. 7 shows an absorption spectrum of 22B (SEQ ID NO: 5)
Figure 8:
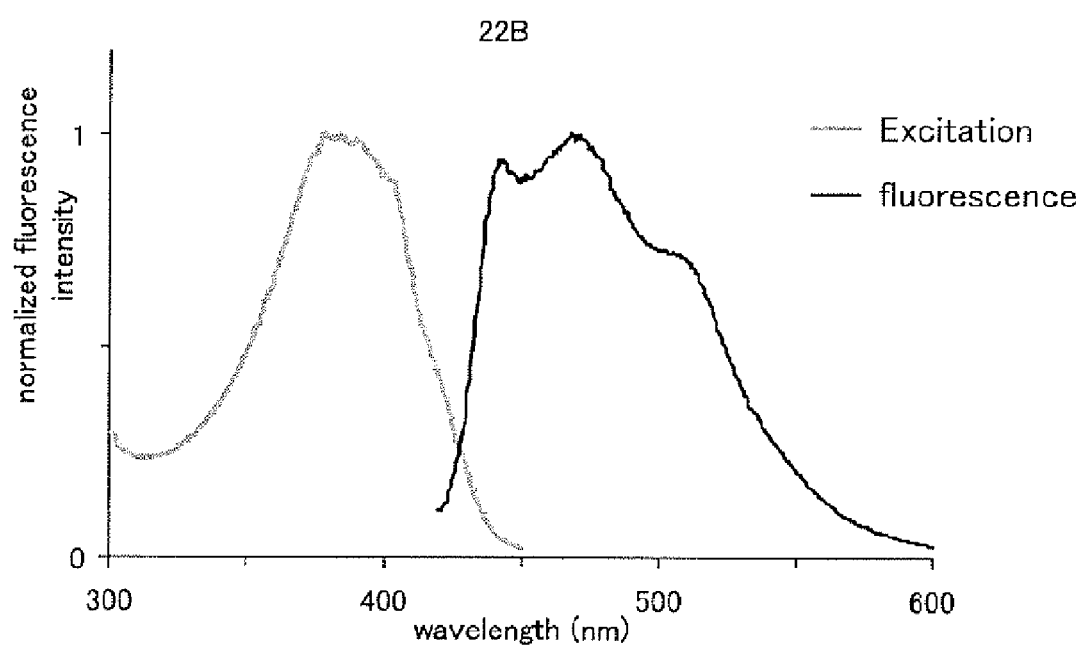
FIG. 8 shows fluorescence and excitation spectra of 22B (SEQ ID NO: 5)

For the absorption spectrum, 50 mM HEPES (pH 7.5) solution was used. For the fluorescence and excitation spectra, 50 mM HEPES (pH 7.5) solution was used, and the fluorescence spectrum excited at 380 nm and the excitation spectrum for 470 nm fluorescence were measured. The absorption spectrum of the fluorescent protein 22B (SEQ ID NO: 5) is shown in FIG. 7, and the fluorescence and excitation spectra are shown in FIG. 8. The absorption maximum is 380 nm, and the fluorescence maximum is 467 nm.

Example 7

Preparation of Mutant of Fluorescent Protein m22G3 (SEQ ID NO: 3)

Mutation was further inserted into the fluorescent protein m22G3 (mutant of the fluorescent protein 22G (SEQ ID NO: 1)) (also referred to as Dronpa) (SEQ ID NO: 3) obtained in Example 3 according to the following procedures, and a mutant having different properties was obtained.
<Method> Random Mutagenesis Mutations were randomly introduced by performing PCR in the presence of added $MnCl_2$ using the DNA of m22G3 (Dronpa) (SEQ ID NO: 4) as the template.

For the DNA polymerase, TAKARA Taq (product of Takara Bio Inc.) was used. A primer with a BamHI site added to the 5' side and a primer with an EcoRI site added to the 3' side were used as the forward primer and the reverse primer, respectively. Amplified DNA was cut with BamHI and EcoRI and then inserted into $pRSET_B$, followed by introduction into the JM109 DE3 strain and culturing on a LA plate.

Among clones obtained by the random mutagenesis, a clone having properties greatly different from those of m22G3 (Dronpa) was selected, and the nucleotide sequence of the clone was determined by a DNA sequencer. This clone was named m3m4. The amino acid sequence and the nucleotide sequence of m3m4 are shown in SEQ ID NOs: 7 and 8, respectively.

Using E. coli, a protein in which a His-tag was added to the fluorescent protein m3m4 (SEQ ID NO: 7) was expressed according to a conventional method and purified with Ni-Agarose.

Example 8

Analysis of Fluorescence Characteristics of Mutant m3m4 (SEQ ID NO: 7)

(1) Absorption Spectrum and Fluorescence and Excitation Spectra

Figure 9:
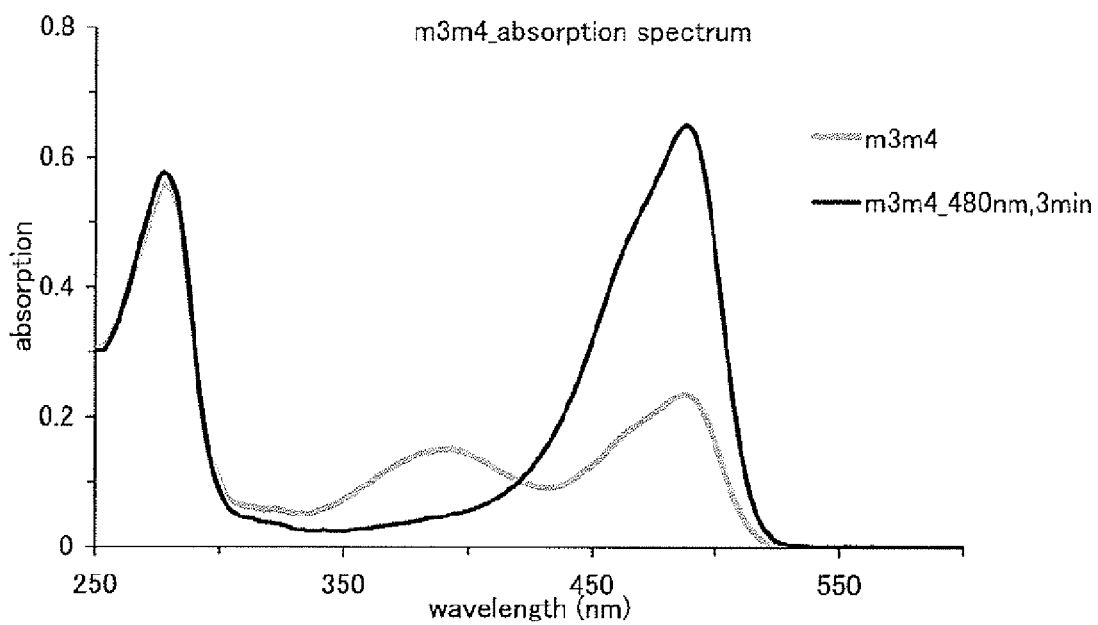
FIG. 9 shows an absorption spectrum of m3m4 (SEQ ID NO: 7)

For the absorption spectrum, 50 mM HEPES (pH 7.5) solution was used (FIG. 9, black). When strong light of 480 nm is irradiated for 3 min, a peak at 486 nm becomes low, and an absorption at 390 nm appears (FIG. 9, gray).

Figure 10:
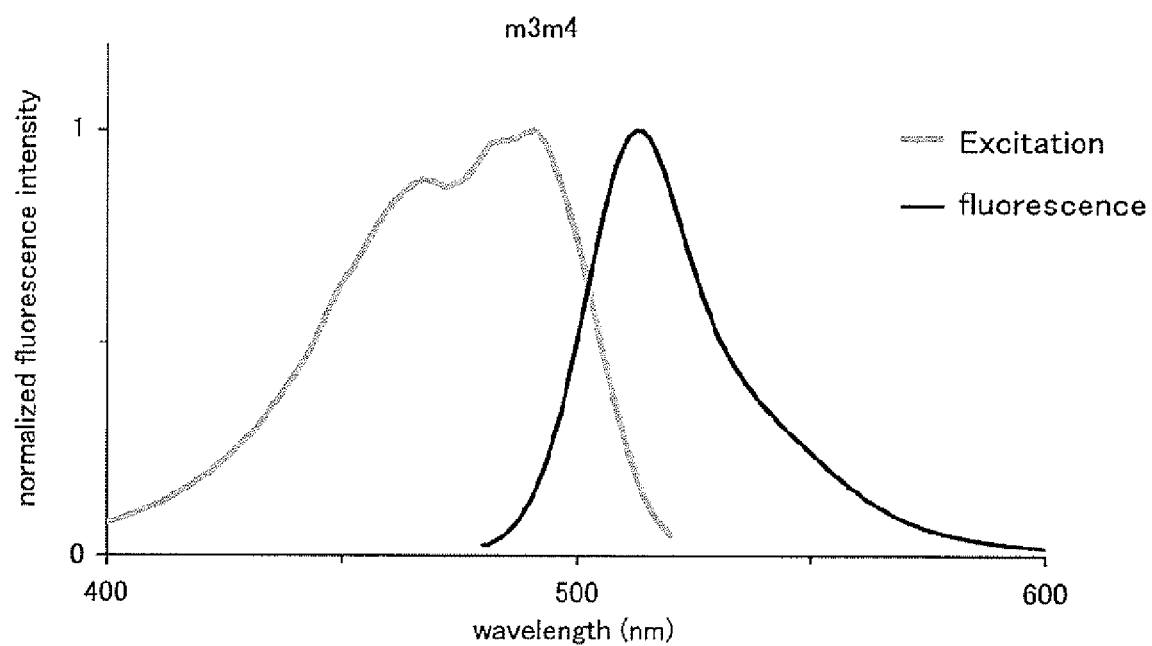
FIG. 10 shows fluorescence and excitation spectra of m3m4 (SEQ ID NO: 7)

For the fluorescence and excitation spectra, 50 mM HEPES (pH 7.5) solution was used, and the fluorescence spectrum excited at 470 nm and the excitation spectrum for 530 nm fluorescence were measured (FIG. 10).

The properties of m3m4 (SEQ ID NO: 7) are shown in Table 3.

TABLE 3

| Absorption maximum | Fluorescence maximum | Molar extinction coefficient ($M^{-1} cm^{-1}$) | Quantum yield |
|---|---|---|---|
| 486 nm | 513 nm | 56,000 (486 nm, pH 7.4) | 0.28 |

(2) Comparison Between m22G3 (Dronpa) (SEQ ID NO: 3) and m3m4 (SEQ ID NO: 7)

When m3m4 (SEQ ID NO: 7) was irradiated with strong light of 480 nm having the same light intensity as that used for m22G3 (Dronpa) (SEQ ID NO: 3), m3m4 (SEQ ID NO: 7) became dark at an approximately 5-fold faster rate. When the darkened m3m4 (SEQ ID NO: 7) was irradiated with light of 400 nm having the same light intensity, m3m4 (SEQ ID NO: 7) was brightened at approximately the same rate (left figure in FIG. 11).

Figure 11:
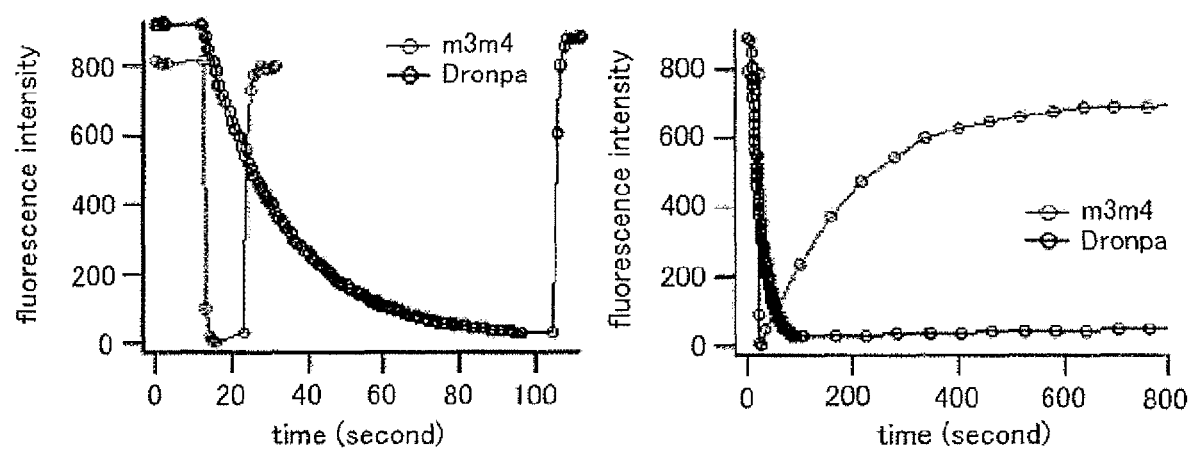
FIG. 11 shows comparison of fluorescence characteristics between m3m4 (SEQ ID NO: 7) and m22G3 (Dronpa) (SEQ ID NO: 3).

In addition, m3m4 (SEQ ID NO: 7) and m22G3 (Dronpa) (SEQ ID NO: 3) that had been darkened with the intense light of 480 nm were left standing for about 10 min at room temperature, m22G3 (Dronpa) (SEQ ID NO: 3) hardly changed, whereas m3m4 (SEQ ID NO: 7) restored approximately 80% of the fluorescence (right figure in FIG. 11).

INDUSTRIAL APPLICABILITY

The fluorescent protein of the present invention is useful as a material for photonics devices in the technical field of information recording or image display, because of its potential to acquire or lose fluorescence by control of light. The fluorescent protein of the present invention can be put to practical use, for example as a rewritable optical memory device. Further, the fluorescent protein or the gene coding therefor of the present invention can be used as a printing material for copy protection, reversible image display medium on which writing and erasing of color image information by light irradiation can be repeatedly performed, hologram material, light shielding material for specific wavelength, material for optical switching device, or the like.

The invention claimed is:

1. A fluorescent protein shown in the following (a) or (b):
   (a) a protein which has the amino acid sequence shown in SEQ ID NO: 3; or
   (b) a protein which has
   an amino acid sequence comprising a deletion, substitution, and/or addition of one to twenty amino acids with respect to the amino acid sequence shown in SEQ ID NO: 3,
   an aspartic acid residue at position 172, a histidine residue at position 194, and a serine residue at position 205 with respect to SEQ ID NO: 3,
   and which has fluorescence characteristics of exhibiting a photochromic effect.

2. A photochromic material comprising the fluorescent protein of claim 1.

3. A DNA encoding the fluorescent protein according to claim 1.

4. A recombinant vector having the DNA of claim 3.

5. An isolated host cell having the DNA of claim 3.

6. An isolated host cell having the recombinant vector of claim 4.

* * * * *

SEQUENCE LISTING

```
<160> NUMBER OF SEQ ID NOS: 11

<210> SEQ ID NO 1
<211> LENGTH: 224
<212> TYPE: PRT
<213> ORGANISM: Echinophylia sp.

<400> SEQUENCE: 1

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Val Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Asn Tyr Glu
                85                  90                  95

Asp Gly Gly Ile Cys Ile Ala Thr Asn Asp Ile Thr Leu Asp Gly Asp
            100                 105                 110

Cys Phe Ile Tyr Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Leu Leu Glu Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His Arg Ile Glu Ile Lys Ser His Asp Lys Asp Tyr Asn Asn Val Asn
        195                 200                 205

Leu His Glu His Ala Glu Ala His Ser Gly Leu Pro Arg Gln Ala Lys
    210                 215                 220

<210> SEQ ID NO 2
<211> LENGTH: 672
<212> TYPE: DNA
<213> ORGANISM: Echinophylia sp.
<220> FEATURE:
<221> NAME/KEY: CDS
<222> LOCATION: (1)..(672)

<400> SEQUENCE: 2 atg agt gtg att aaa cca gac atg aag atc aag ctg cgt atg gaa ggc      48
Met Ser Val Ile Lys Pro Asp Met Lys Ile Lys Leu Arg Met Glu Gly
1               5                   10                  15 gct gta aat gga cac ccg ttc gcg att gaa gga gtt ggc ctt ggg aag      96
```

| | | | | | | | | | | | | | | | |
|---|---|---|---|---|---|---|---|---|---|---|---|---|---|---|---|
|Ala|Val|Asn|Gly|His|Pro|Phe|Ala|Ile|Glu|Gly|Val|Gly|Leu|Gly|Lys|
| | | |20 | | |  |25| | | |  |30| | | |

```
cct ttc gag gga aaa cag agt atg gac ctt aaa gtc aaa gaa ggc gga      144
Pro Phe Glu Gly Lys Gln Ser Met Asp Leu Lys Val Lys Glu Gly Gly
         35                  40                  45 cct ctg cct ttc gcc tat gac atc ttg aca aca gtg ttc tgt tac ggc      192
Pro Leu Pro Phe Ala Tyr Asp Ile Leu Thr Thr Val Phe Cys Tyr Gly
 50                  55                  60 aac agg gta ttc gcc aaa tac cca gaa aat ata gta gac tat ttc aag      240
Asn Arg Val Phe Ala Lys Tyr Pro Glu Asn Ile Val Asp Tyr Phe Lys
 65                  70                  75                  80 cag tcg ttt cct gag ggc tac tct tgg gaa cga agc atg aat tac gaa      288
Gln Ser Phe Pro Glu Gly Tyr Ser Trp Glu Arg Ser Met Asn Tyr Glu
                 85                  90                  95 gac ggg ggc att tgt atc gcg aca aac gac ata acc ctg gat ggt gac      336
Asp Gly Gly Ile Cys Ile Ala Thr Asn Asp Ile Thr Leu Asp Gly Asp
            100                 105                 110 tgt ttt atc tat gaa att cga ttt gat ggt gtg aac ttt cct gcc aat      384
Cys Phe Ile Tyr Glu Ile Arg Phe Asp Gly Val Asn Phe Pro Ala Asn
        115                 120                 125 ggt cca gtt atg cag aag agg act gtg aaa tgg gag cca tcc act gag      432
Gly Pro Val Met Gln Lys Arg Thr Val Lys Trp Glu Pro Ser Thr Glu
130                 135                 140 aaa ttg tat gtg cgt gat gga gtg ctg aag ggt gat gtt aac atg gct      480
Lys Leu Tyr Val Arg Asp Gly Val Leu Lys Gly Asp Val Asn Met Ala
145                 150                 155                 160 ctg ttg ctt gaa gga ggt ggc cat tac cga tgt gac ttc aaa act act      528
Leu Leu Leu Glu Gly Gly Gly His Tyr Arg Cys Asp Phe Lys Thr Thr
                165                 170                 175 tat aaa gct aag aag gtt gtc cag ttg cca gac tat cac ttt gtg gac      576
Tyr Lys Ala Lys Lys Val Val Gln Leu Pro Asp Tyr His Phe Val Asp
            180                 185                 190 cac cgc att gag att aaa agc cac gac aaa gat tac aat aat gtt aat      624
His Arg Ile Glu Ile Lys Ser His Asp Lys Asp Tyr Asn Asn Val Asn
        195                 200                 205 ctg cat gag cat gcc gaa gcg cat tct ggg ctg ccg agg cag gcc aag      672
Leu His Glu His Ala Glu Ala His Ser Gly Leu Pro Arg Gln Ala Lys
210                 215                 220
```

<210> SEQ ID NO 3
<211> LENGTH: 224
<212> TYPE: PRT
<213> ORGANISM: Echinophylia sp.

<400> SEQUENCE: 3

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Val Phe Cys Tyr Gly
 50                  55                  60

Asn Arg Val Phe Ala Lys Tyr Pro Glu Asn Ile Val Asp Tyr Phe Lys
 65                  70                  75                  80

Gln Ser Phe Pro Glu Gly Tyr Ser Trp Glu Arg Ser Met Asn Tyr Glu
                 85                  90                  95

Asp Gly Gly Ile Cys Asn Ala Thr Asn Asp Ile Thr Leu Asp Gly Asp
            100                 105                 110

```
Cys Tyr Ile Tyr Glu Ile Arg Phe Asp Gly Val Asn Phe Pro Ala Asn
            115                 120                 125

Gly Pro Val Met Gln Lys Arg Thr Val Lys Trp Glu Pro Ser Thr Glu
130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His His Ile Glu Ile Lys Ser Asp Lys Asp Tyr Ser Asn Val Asn
            195                 200                 205

Leu His Glu His Ala Glu Ala His Ser Glu Leu Pro Arg Gln Ala Lys
210                 215                 220
```

<210> SEQ ID NO 4
<211> LENGTH: 672
<212> TYPE: DNA
<213> ORGANISM: Echinophylia sp.
<220> FEATURE:
<221> NAME/KEY: CDS
<222> LOCATION: (1)..(672)

<400> SEQUENCE: 4

```
atg agt gtg att aaa cca gac atg aag atc aag ctg cgt atg gaa ggc      48
Met Ser Val Ile Lys Pro Asp Met Lys Ile Lys Leu Arg Met Glu Gly
1               5                   10                  15 gct gta aat gga cac ccg ttc gcg att gaa gga gtt ggc ctt ggg aag      96
Ala Val Asn Gly His Pro Phe Ala Ile Glu Gly Val Gly Leu Gly Lys
                20                  25                  30 cct ttc gag gga aaa cag agt atg gac ctt aaa gtc aaa gaa ggc gga     144
Pro Phe Glu Gly Lys Gln Ser Met Asp Leu Lys Val Lys Glu Gly Gly
            35                  40                  45 cct ctg cct ttc gcc tat gac atc ttg aca act gtg ttc tgt tac ggc     192
Pro Leu Pro Phe Ala Tyr Asp Ile Leu Thr Thr Val Phe Cys Tyr Gly
        50                  55                  60 aac agg gta ttc gcc aaa tac cca gaa aat ata gta gac tat ttc aag     240
Asn Arg Val Phe Ala Lys Tyr Pro Glu Asn Ile Val Asp Tyr Phe Lys
65                  70                  75                  80 cag tcg ttt cct gag ggc tac tct tgg gaa cga agc atg aat tac gaa     288
Gln Ser Phe Pro Glu Gly Tyr Ser Trp Glu Arg Ser Met Asn Tyr Glu
                85                  90                  95 gac ggg ggc att tgt aac gcg aca aac gac ata acc ctg gat ggt gac     336
Asp Gly Gly Ile Cys Asn Ala Thr Asn Asp Ile Thr Leu Asp Gly Asp
                100                 105                 110 tgt tat atc tat gaa att cga ttt gat ggt gtg aac ttt cct gcc aat     384
Cys Tyr Ile Tyr Glu Ile Arg Phe Asp Gly Val Asn Phe Pro Ala Asn
            115                 120                 125 ggt cca gtt atg cag aag agg act gtg aaa tgg gag cca tcc act gag     432
Gly Pro Val Met Gln Lys Arg Thr Val Lys Trp Glu Pro Ser Thr Glu
        130                 135                 140 aaa ttg tat gtg cgt gat gga gtg ctg aag ggt gat gtt aac atg gct     480
Lys Leu Tyr Val Arg Asp Gly Val Leu Lys Gly Asp Val Asn Met Ala
145                 150                 155                 160 ctg tcg ctt gaa gga ggt ggc cat tac cga tgt gac ttc aaa act act     528
Leu Ser Leu Glu Gly Gly Gly His Tyr Arg Cys Asp Phe Lys Thr Thr
                165                 170                 175 tat aaa gct aag aag gtt gtc cag ttg cca gac tat cac ttt gtg gac     576
Tyr Lys Ala Lys Lys Val Val Gln Leu Pro Asp Tyr His Phe Val Asp
            180                 185                 190
```

| | | |
|---|---|---|
| cac cac att gag att aaa agc cac gac aaa gat tac agt aat gtt aat<br>His His Ile Glu Ile Lys Ser His Asp Lys Asp Tyr Ser Asn Val Asn<br>                195                    200                    205 | | 624 |
| ctg cat gag cat gcc gaa gcg cat tct gag ctg ccg agg cag gcc aag<br>Leu His Glu His Ala Glu Ala His Ser Glu Leu Pro Arg Gln Ala Lys<br>                210                    215                    220 | | 672 |

<210> SEQ ID NO 5
<211> LENGTH: 224
<212> TYPE: PRT
<213> ORGANISM: Echinophylia sp.

<400> SEQUENCE: 5

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
                20                  25                  30

Pro Phe Glu Gly Lys Gln Ser Met Asp Leu Lys Val Lys Glu Gly Gly
            35                  40                  45

Pro Leu Pro Phe Ala Tyr Asp Ile Leu Thr Thr Ala Phe Cys His Gly
        50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Asn Tyr Glu
                85                  90                  95

Asp Gly Gly Ile Cys Asn Ala Thr Asn Asp Ile Thr Leu Asp Gly Asp
            100                 105                 110

Cys Tyr Ile Tyr Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

Arg Arg Ile Glu Ile Lys Ser His Asp Lys Asp Tyr Asn Asn Val Asn
        195                 200                 205

Leu His Glu His Ala Glu Ala His Ser Gly Leu Pro Arg Gln Ala Lys
    210                 215                 220

<210> SEQ ID NO 6
<211> LENGTH: 672
<212> TYPE: DNA
<213> ORGANISM: Echinophylia sp.
<220> FEATURE:
<221> NAME/KEY: CDS
<222> LOCATION: (1)..(672)

<400> SEQUENCE: 6

| | | |
|---|---|---|
| atg agt gtg att aaa cca gac atg aag atc aag ctg cgt atg gaa ggc<br>Met Ser Val Ile Lys Pro Asp Met Lys Ile Lys Leu Arg Met Glu Gly<br>1                    5                      10                    15 | | 48 |
| gct gta aat gga cac ccg ttc gcg att gaa gga gtt ggc ctt ggg aag<br>Ala Val Asn Gly His Pro Phe Ala Ile Glu Gly Val Gly Leu Gly Lys<br>                20                    25                    30 | | 96 |
| cct ttc gag gga aaa cag agt atg gac ctt aaa gtc aaa gaa ggc gga<br>Pro Phe Glu Gly Lys Gln Ser Met Asp Leu Lys Val Lys Glu Gly Gly<br>           35                    40                    45 | | 144 |

-continued

```
cct ctg cct ttc gcc tat gac atc ttg aca aca gcg ttc tgt cac ggc        192
Pro Leu Pro Phe Ala Tyr Asp Ile Leu Thr Thr Ala Phe Cys His Gly
     50                  55                  60 aac agg gta ttc gcc aaa tac cca gaa aat ata gta gac tat ttc aag        240
Asn Arg Val Phe Ala Lys Tyr Pro Glu Asn Ile Val Asp Tyr Phe Lys
 65                  70                  75                  80 cag tcg ttt cct gag ggc tac tct tgg gaa cga agc atg aat tac gaa        288
Gln Ser Phe Pro Glu Gly Tyr Ser Trp Glu Arg Ser Met Asn Tyr Glu
             85                  90                  95 gac ggg ggc att tgt aac gcg aca aac gac ata acc ctg gat ggt gac        336
Asp Gly Gly Ile Cys Asn Ala Thr Asn Asp Ile Thr Leu Asp Gly Asp
         100                 105                 110 tgt tat atc tat gaa att cga ttt gat ggt gtg aac ttt cct gcc aat        384
Cys Tyr Ile Tyr Glu Ile Arg Phe Asp Gly Val Asn Phe Pro Ala Asn
     115                 120                 125 ggt cca gtt atg cag aag agg act gtg aaa tgg gag cca tcc act gag        432
Gly Pro Val Met Gln Lys Arg Thr Val Lys Trp Glu Pro Ser Thr Glu
 130                 135                 140 aaa ttg tat gtg cgt gat gga gtg ctg aag ggt gat gtt aac atg gct        480
Lys Leu Tyr Val Arg Asp Gly Val Leu Lys Gly Asp Val Asn Met Ala
145                 150                 155                 160 ctg tcg ctt gaa gga ggt ggc cat tac cga tgt gac ttc aaa act act        528
Leu Ser Leu Glu Gly Gly Gly His Tyr Arg Cys Asp Phe Lys Thr Thr
             165                 170                 175 tat aaa gct aag aag gtt gtc cag ttg cca gac tat cac ttt gtg gac        576
Tyr Lys Ala Lys Lys Val Val Gln Leu Pro Asp Tyr His Phe Val Asp
         180                 185                 190 cgc cgc att gag att aaa agc cac gac aaa gat tac aat aat gtt aat        624
Arg Arg Ile Glu Ile Lys Ser His Asp Lys Asp Tyr Asn Asn Val Asn
     195                 200                 205 ctg cat gag cat gcc gaa gcg cat tct ggc ctg ccg agg cag gcc aag        672
Leu His Glu His Ala Glu Ala His Ser Gly Leu Pro Arg Gln Ala Lys
 210                 215                 220
```

<210> SEQ ID NO 7
<211> LENGTH: 224
<212> TYPE: PRT
<213> ORGANISM: Echinophylia sp.

<400> SEQUENCE: 7

```
Met Ser Val Ile Lys Pro Asp Met Lys Ile Lys Leu Arg Met Glu Gly
  1               5                  10                  15

Ala Val Asn Gly His Pro Phe Ala Ile Glu Gly Val Gly Leu Gly Lys
             20                  25                  30

Pro Phe Glu Gly Lys Gln Ser Met Asp Leu Lys Val Lys Glu Gly Gly
         35                  40                  45

Pro Leu Pro Phe Ala Tyr Asp Ile Leu Thr Thr Val Phe Cys Tyr Gly
     50                  55                  60

Asn Arg Val Phe Ala Lys Tyr Pro Glu Asn Ile Val Asp Tyr Phe Lys
 65                  70                  75                  80

Gln Ser Phe Pro Glu Gly Tyr Ser Trp Glu Arg Ser Met Asn Tyr Glu
             85                  90                  95

Asp Gly Gly Ile Cys Asn Ala Thr Asn Asp Ile Thr Leu His Gly Asp
         100                 105                 110

Cys Tyr Ile Tyr Glu Ile Arg Phe Asp Gly Val Asn Phe Pro Ala Asn
     115                 120                 125

Gly Pro Val Met Gln Lys Arg Thr Val Lys Trp Glu Pro Ser Thr Glu
 130                 135                 140
```

```
Lys Leu Tyr Val Arg Asp Gly Val Leu Lys Gly Asp Val Asn Thr Ala
145                 150                 155                 160

Leu Ser Leu Glu Gly Gly His Tyr Arg Cys Val Phe Lys Thr Thr
            165                 170                 175

Tyr Lys Ala Lys Arg Val Val Gln Leu Pro Asp Tyr His Phe Val Asp
            180                 185                 190

His His Ile Glu Ile Lys Ser His Asp Lys Asp Tyr Ser Asn Val Asn
            195                 200                 205

Leu His Glu His Ala Glu Ala His Ser Glu Leu Pro Arg Gln Ala Lys
210                 215                 220

<210> SEQ ID NO 8
<211> LENGTH: 672
<212> TYPE: DNA
<213> ORGANISM: Echinophylia sp.
<220> FEATURE:
<221> NAME/KEY: CDS
<222> LOCATION: (1)..(672)

<400> SEQUENCE: 8 atg agt gtg att aaa cca gac atg aag atc aag ctg cgt atg gaa ggc    48
Met Ser Val Ile Lys Pro Asp Met Lys Ile Lys Leu Arg Met Glu Gly
1               5                   10                  15 gct gta aat gga cac ccg ttc gcg att gaa gga gtt ggc ctt ggg aag    96
Ala Val Asn Gly His Pro Phe Ala Ile Glu Gly Val Gly Leu Gly Lys
            20                  25                  30 cct ttc gag gga aaa cag agt atg gac ctt aaa gtc aaa gaa ggc gga   144
Pro Phe Glu Gly Lys Gln Ser Met Asp Leu Lys Val Lys Glu Gly Gly
        35                  40                  45 cct ctg cct ttc gcc tat gac atc ttg aca act gtg ttc tgt tac ggc   192
Pro Leu Pro Phe Ala Tyr Asp Ile Leu Thr Thr Val Phe Cys Tyr Gly
50                  55                  60 aac agg gta ttc gcc aaa tac cca gaa aat ata gta gac tat ttc aag   240
Asn Arg Val Phe Ala Lys Tyr Pro Glu Asn Ile Val Asp Tyr Phe Lys
65                  70                  75                  80 cag tcg ttt cct gag ggc tac tct tgg gaa cga agc atg aat tac gaa   288
Gln Ser Phe Pro Glu Gly Tyr Ser Trp Glu Arg Ser Met Asn Tyr Glu
                85                  90                  95 gac ggg ggc att tgt aac gcg aca aac gac ata acc ctc cat ggt gac   336
Asp Gly Gly Ile Cys Asn Ala Thr Asn Asp Ile Thr Leu His Gly Asp
            100                 105                 110 tgt tat atc tat gaa att cga ttt gat ggt gtg aac ttt cct gcc aat   384
Cys Tyr Ile Tyr Glu Ile Arg Phe Asp Gly Val Asn Phe Pro Ala Asn
        115                 120                 125 ggt cca gtt atg cag aag agg act gtg aaa tgg gag cca tcc act gag   432
Gly Pro Val Met Gln Lys Arg Thr Val Lys Trp Glu Pro Ser Thr Glu
130                 135                 140 aaa ttg tat gtg cgt gat gga gtg ctg aag ggt gat gtt aac acg gct   480
Lys Leu Tyr Val Arg Asp Gly Val Leu Lys Gly Asp Val Asn Thr Ala
145                 150                 155                 160 ctg tcg ctt gaa gga ggt ggc cat tac cga tgt gtc ttc aaa act act   528
Leu Ser Leu Glu Gly Gly Gly His Tyr Arg Cys Val Phe Lys Thr Thr
            165                 170                 175 tat aaa gct aag agg gtt gtc cag ttg cca gac tat cac ttt gtg gac   576
Tyr Lys Ala Lys Arg Val Val Gln Leu Pro Asp Tyr His Phe Val Asp
        180                 185                 190 cac cac att gag att aaa agc cac gac aaa gat tac agt aat gtt aat   624
His His Ile Glu Ile Lys Ser His Asp Lys Asp Tyr Ser Asn Val Asn
            195                 200                 205 ctg cat gag cat gcc gaa gcg cat tct gag ctg ccg agg cag gcc aag   672
Leu His Glu His Ala Glu Ala His Ser Glu Leu Pro Arg Gln Ala Lys
```

-continued

```
<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aactggaaga attcgcggcc gcaggaattt ttttttttt ttttt              45

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagctcccgg atccgatgag tgtgattaaa ccagac                       36

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcgttgaat tcttacttgg cctgcctcgg cag                          33
```